(12) United States Patent
Benoit et al.

(10) Patent No.: US 7,505,123 B2
(45) Date of Patent: *Mar. 17, 2009

(54) LIGHT DELIVERY CONTROL SYSTEM AND METHOD

(75) Inventors: Jeffrey T. Benoit, Willington, CT (US); Wayde R. Schmidt, Pomfret Center, CT (US); Thomas H. Vanderspurt, Glastonbury, CT (US)

(73) Assignee: Carrier Corporation, Syracuse, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/927,731

(22) Filed: Oct. 30, 2007

(65) Prior Publication Data

US 2008/0049432 A1  Feb. 28, 2008

Related U.S. Application Data

(63) Continuation of application No. 10/827,655, filed on Apr. 19, 2004, now Pat. No. 7,307,704.

(51) Int. Cl.
*G01N 21/00* (2006.01)
*G01J 1/20* (2006.01)
*G02B 6/34* (2006.01)

(52) U.S. Cl. .................. 356/73; 250/228; 250/359.1; 250/201.9; 385/89.8; 422/121

(58) Field of Classification Search ............. 356/72–73; 250/341, 359.1; 362/290–291, 354, 342; 378/98.2, 98.8; 385/37, 40; 204/157.15, 204/157.3
See application file for complete search history.

(56) References Cited

U.S. PATENT DOCUMENTS

| | | | |
|---|---|---|---|
| 3,559,555 A | 2/1971 | Street | |
| 3,838,908 A | 10/1974 | Channin | |
| 4,339,170 A | 7/1982 | Winzer | |
| 4,351,585 A | 9/1982 | Winzer | |
| 4,506,275 A | 3/1985 | Maeda | |
| 5,019,710 A | 5/1991 | Wennerberg | |
| 5,299,570 A | 4/1994 | Hatschek | |
| 5,559,850 A | 9/1996 | Nekovar | |
| 5,919,422 A | 7/1999 | Yamanaka | |
| 6,238,630 B1 | 5/2001 | Iimura | |
| 6,278,100 B1 | 8/2001 | Friedman | |
| 6,309,611 B1 | 10/2001 | Tabatabaie-Raissi | |
| 6,457,844 B2 | 10/2002 | Hess | |
| 6,902,653 B2 * | 6/2005 | Carmignani et al. ... | 204/157.15 |
| 6,995,355 B2 | 2/2006 | Rains | |

OTHER PUBLICATIONS

International Search Report Dated Dec. 18, 2006 *References 3,838,908; 5,559,850; 5,299,570 cited by examiner*.

* cited by examiner

*Primary Examiner*—Sang Nguyen
(74) *Attorney, Agent, or Firm*—Carlson, Gaskey & Olds

(57) ABSTRACT

A method that redistributes light from a light source. The controller can redistribute light to make an irradiance profile of the light source more uniform or make the irradiance profile match a fluid flow profile. The irradiance profile may be controlled by modifying light leakage from a plurality of waveguides or changing the light-directing properties of reflectors and/or lenses.

19 Claims, 5 Drawing Sheets

LIGHT DELIVERY CONTROL SYSTEM AND METHOD

RELATED APPLICATION

This application is a continuation U.S. patent application Ser. No. 10/827,655, now U.S. Pat. No. 7,307,704 which was filed Apr. 19, 2004.

TECHNICAL FIELD

The present invention relates to controlling light delivery to improve uniformity and/or an irradiance profile of delivered light.

BACKGROUND OF THE INVENTION

Duct structures and other items allowing fluid flow may have photocatalyst material disposed on the surface to be activated by light from a light delivery system. The efficiency of the photoreactor depends in part on the uniformity of the light illuminating the item as well as the correspondence between the fluid flow profile and an irradiation profile of the light generated by the light delivery system. However, the geometric differences between the shape of the light source and the shape of the surface being illuminated may naturally cause some surfaces to receive more light than other surfaces (e.g., surfaces closer to the light source will have more illumination than surfaces farther from the light source).

Further, the system ideally matches the irradiation profile to the fluid flow profile. A non-uniform irradiance profile and/or a lack of a match between the irradiation profile and the fluid flow profile may result in less than optimum utilization of light energy. Areas experiencing excess fluid flow with respect to the irradiance profile, for example, will have excess target chemical species without sufficient photons in the emitted light to catalyze them. Similarly, areas experiencing low fluid flow will have fewer target chemical species than photons in the emitted light, thus wasting photons. This suboptimal reactor efficiency occurs regardless of the specific method used to guide photons from the light source (e.g., free-space delivery, total internal reflection, etc.).

There is a desire for a light delivery system and method that can improve the efficiency of photoreactors.

SUMMARY OF THE INVENTION

The present invention is directed to a system and method that controls light delivery to an object using a light distributor that redistributes light from a light source. This light distributor can be passive or, in the alternative, actively controlled by electronic circuitry or a microprocessor. The light distributor can redistribute light to make an irradiance profile of the light more uniform or, if the light source is in a photoreactor, to make the irradiance profile match a fluid flow profile in the reactor and/or generate light having a uniform irradiation profile.

In one embodiment, the irradiance profile may be controlled by modifying light leakage from a plurality of waveguides. The light leakage characteristics of a given waveguide may be modified by changing the radius of curvature of the waveguide, changing the cross-sectional dimension of the waveguide, changing the refractive index of a cladding on the waveguide, altering a surface roughness of the waveguide, and/or varying the density and/or size of scattering centers in the waveguide.

In another embodiment, the irradiance profile may be controlled by changing the light-directing properties of reflectors and/or lenses. The controller may, for example, change the orientation or shape of one or more reflectors or lenses.

Regardless of the specific way in which light is controlled, the invention can redirect light to areas that are far enough from the light source to experience reduced amounts of light, making the light distribution, and therefore the irradiance profile reflecting the distribution, more uniform over a desired space. Further, the invention can also control light based on received fluid flow data to match the irradiance profile to the fluid flow, increasing reactor efficiency.

DETAILED DESCRIPTION OF THE EMBODIMENTS

Figure 1:
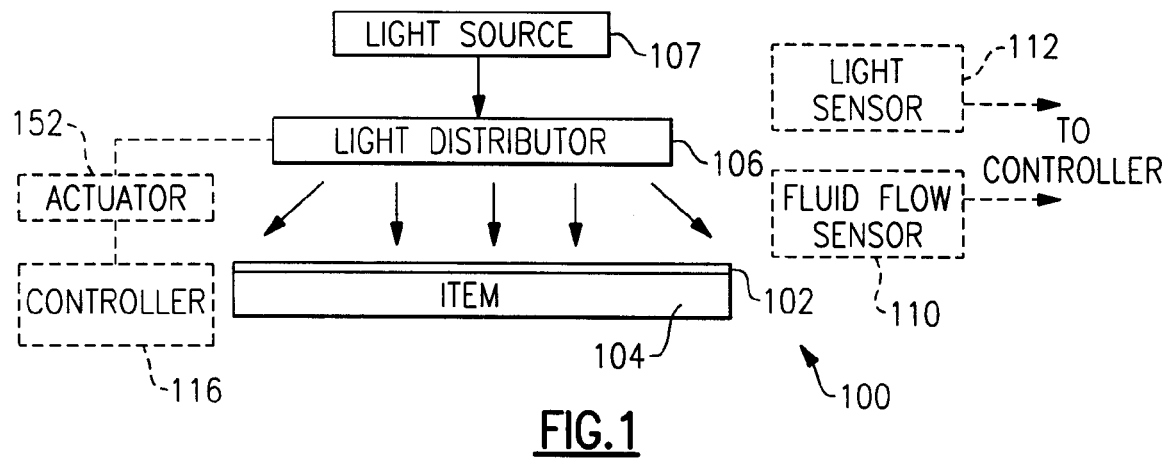
FIG. 1 is a representative diagram of a side view of a photoreactor incorporating the invention.

FIG. 1 is a representative diagram of a photoreactor 100 that can incorporate various embodiments of the invention. The photoreactor 100 is used to, for example, catalyze a photocatalytic surface coating 102 on an HVAC duct or other substrate 104, such as a honeycomb structure. The photocatalytic surface coating 102 catalyzes the desired chemical reactions when a light distributor 106 distributes light from a light source 107, thus illuminating the coating with light energy (e.g., visible light, UV light, etc.) in the presence of the target chemical species within the photoreactor 100. The light distributor 106 and light source 107 can be completely separate from each other or can be integrated together into a single component.

In one embodiment, an optional fluid flow sensor 110 is disposed in the photoreactor 100 to monitor the flow of fluid (e.g., air or other fluid that contains chemicals to be reacted in the photoreactor) and one or more optional light sensors 112 that monitor the irradiation profile of the light energy from the light source 107. The data from the sensors 110, 112 may then be sent to a processor 114 for analysis. The fluid flow sensor 110 can be any device or devices that directly measure fluid flow. Alternatively, the fluid flow sensor 110 can be any device or combination of measurement devices that measure reactor operating conditions (e.g., duct damper positions, air speed, etc) from which the fluid flow can be estimated or inferred.

Note that the sensors 110, 112 may be eliminated if the fluid flow profile is already known or can be adequately estimated based on the operating conditions and characteristics of the system 100. The light distributor 106 may have characteristics that passively redistribute light to make the irradiance profile of the light reaching the photocatalyst 102 uniform and/or to match the irradiation profile with the fluid flow profile. In matching the irradiation profile with the fluid flow profile, it may be assumed that the contaminant profile (i.e., the profile of the chemical species to be reacted) is proportional to the fluid flow profile. This is because, in most cases, the contaminant concentration within the fluid will be constant within different areas of the fluid. Thus, the amount of contaminants flowing past a given point in the photoreactor will be proportional to the volume of fluid flowing past that point.

Alternatively, based on the information from the sensors 110, 112, the processor 114 may also output signals to a controller 116 that actively controls the light distributor 106 to redistribute light based on the data received from the processor 114 to change the irradiance profile of the light radiating on the photocatalyst 102, if needed. This embodiment allows active, dynamic control over the distributing properties of the light distributor 106.

Figure 7:
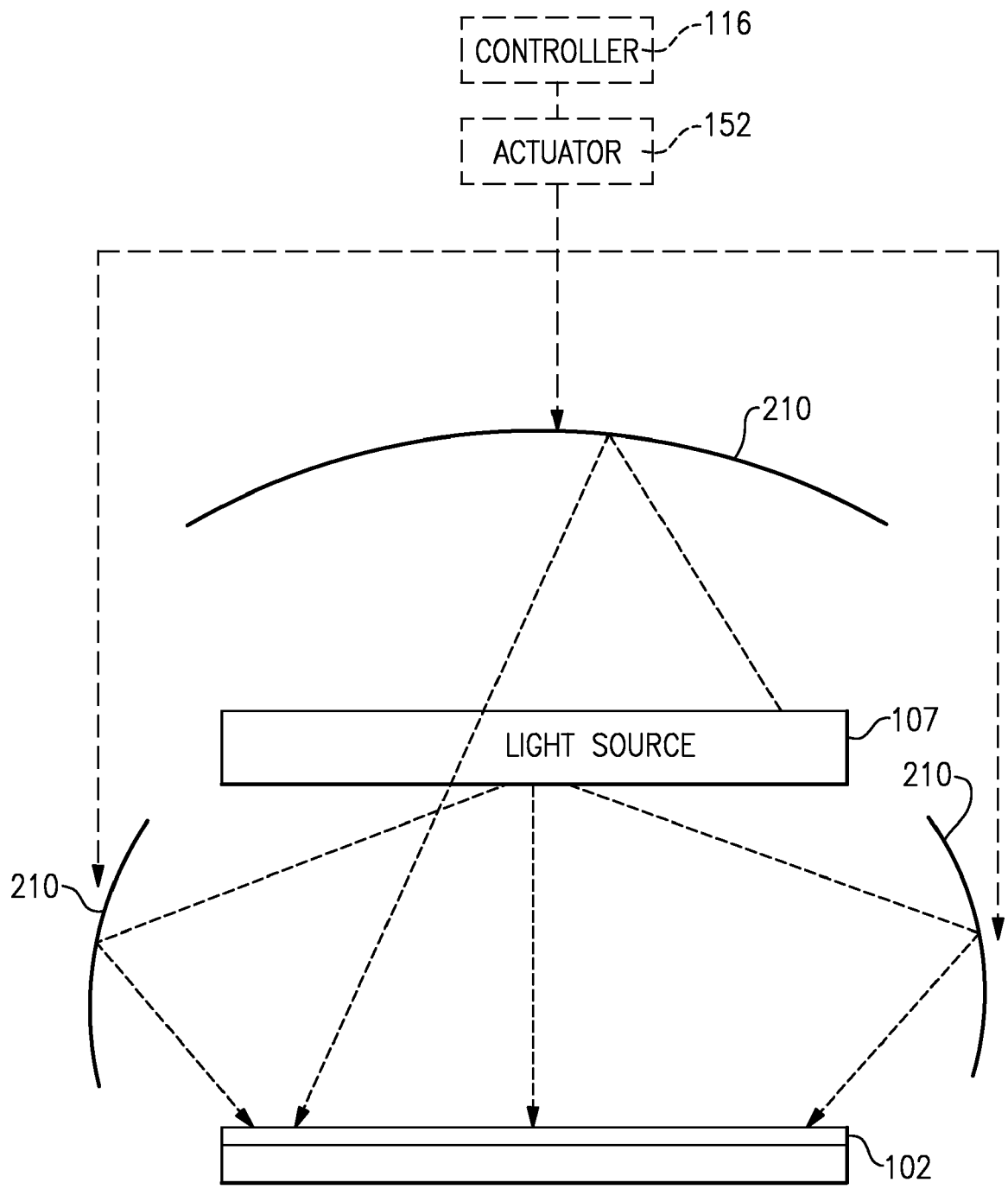
FIG. 7 is a representative diagram of further embodiment of the invention.
Figure 8:
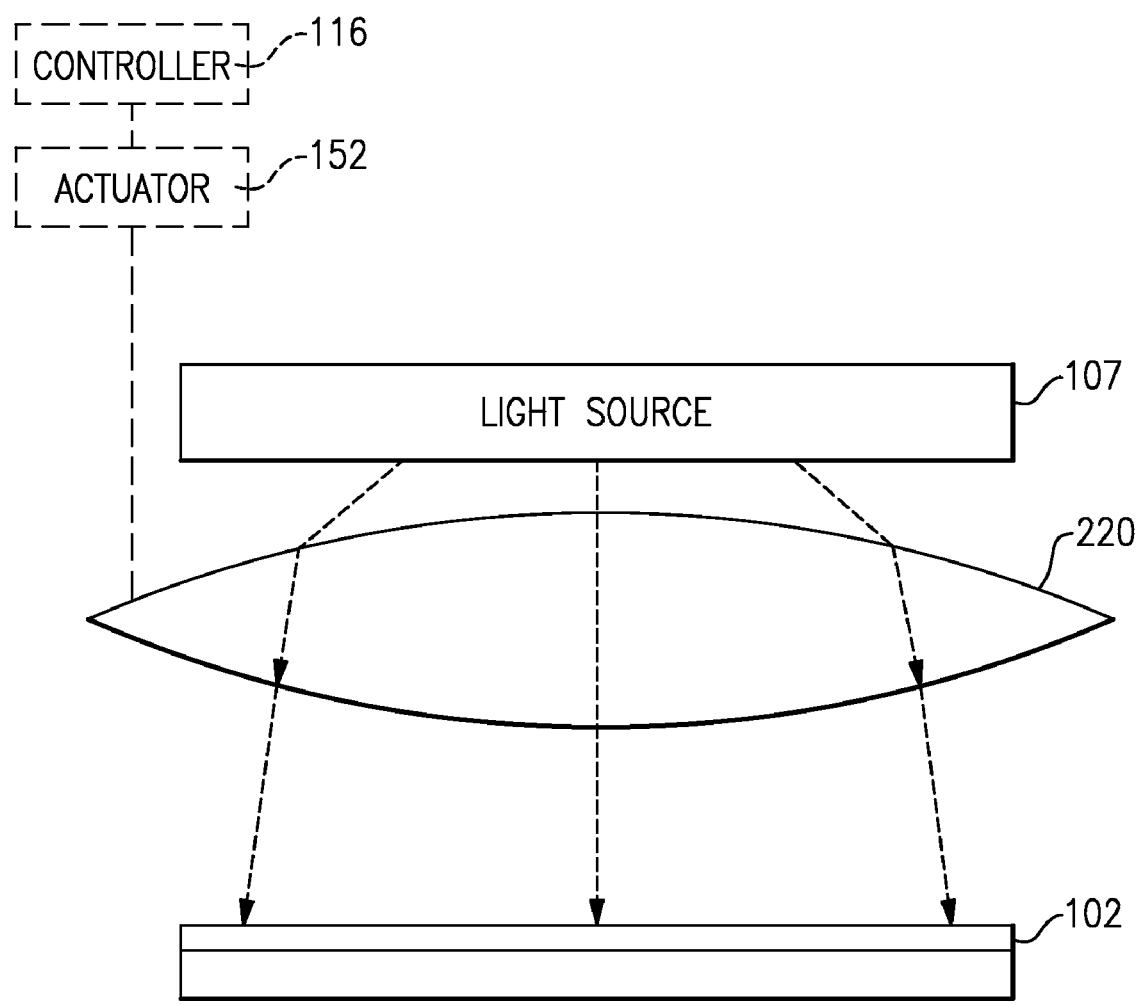
FIG. 8 is a representative diagram of yet another embodiment of the invention.

The remaining figures and the descriptions below describe different structures for the light distributor 106 and the different ways that the light distributor 106 makes the irradiance profile more uniform and/or to match the irradiance profile with the fluid flow profile. The invention is directed to a light distributor 106 that changes the irradiance profile of light reaching the photocatalyst 102. The light distributor 106 can have various structures. In the examples described below, FIGS. 2 through 6 show embodiments where the light distributor 106 is one or more waveguides, FIG. 7 shows an embodiment where the light distributor 106 is one or more reflectors, and FIG. 8 shows an embodiment where the light distributor 106 is one or more lenses.

Figure 2:
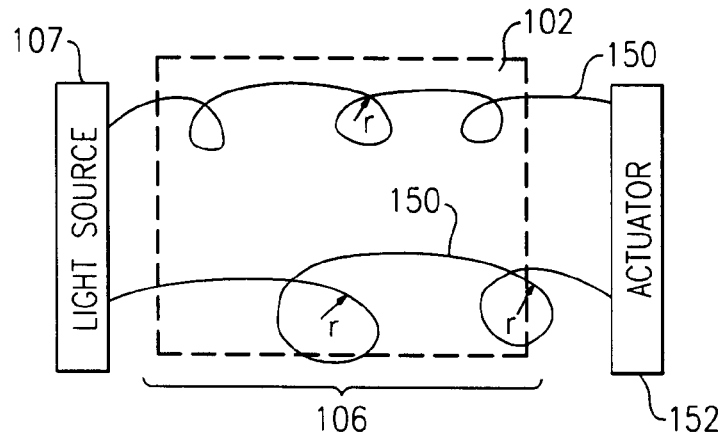
FIG. 2 is a representative diagram of a top view of an embodiment of the invention.

FIG. 2 is a representative diagram of a top view of one embodiment of the light distribution system according to the present invention. As is known in the art, optical waveguides operate on the principle of total internal reflection, where a critical angle $\Theta_c$ at which incident light will be reflected internally in the waveguide is defined $\Theta_c = \arcsin(N_2/N_1)$, where $N_1$ is the refractive index of the waveguide core and $N_2$ is the refractive index of the waveguide cladding. Changing the angle at which incident light strikes the core/cladding interface is one method of controlling the amount of light reflected in and leaking out of the waveguide.

Figure 4:
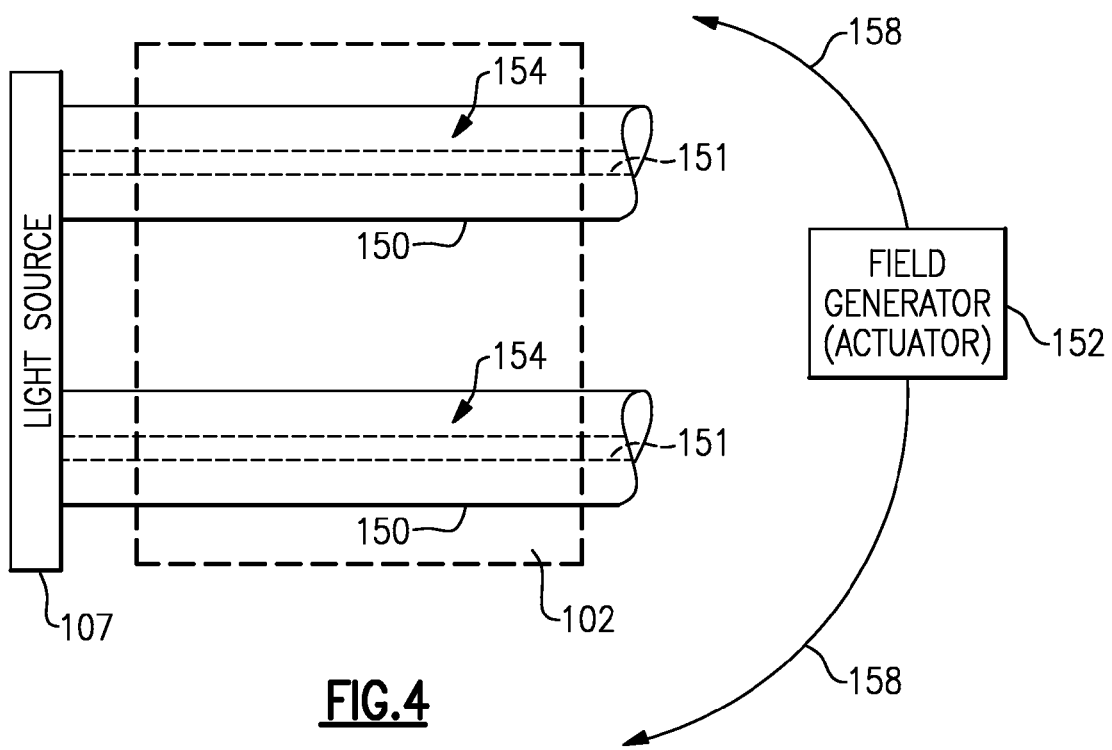
FIG. 4 is a representative diagram of a further embodiment of the invention.

In this embodiment, a plurality of optical waveguides 150 act as the light distributor to control light delivery from the light source 107 to the photocatalyst 102. For total internal reflection waveguides, such as photocatalyst-coated glass, for example, the light leakage from the waveguide 150 is a function of the angle of incidence of the light beam at an interface between a core 151 of the waveguide and its cladding 154 as well as the incident irradiance of the light beam. A more detailed example of the core 151 and cladding 154 configuration is illustrated in FIG. 4 for reference.

In some cases, the irradiance profile may be highest at locations closest to the light source 107. To make the irradiance profile in the reactor 100 more uniform, the curvature of the waveguides 150 can be varied to change the light leakage characteristics of the waveguide to increase the light leakage at areas that are further away from the light source 107. In the illustrated embodiment, the waveguides 150 are curled to change the angle at which light in the waveguide strikes the core/cladding interface and provide a selected amount of light leakage from the waveguide. Areas that are further away from the light source 107 may be bent to have a smaller radius of curvature r to allow greater light leakage. This will balance the irradiance profile and achieve a uniform leakage irradiance over the entire photocatalyst 102.

Alternatively or additionally, the radius of curvature r of the waveguides 150 may be decreased in areas where the fluid flow sensor 110 detects a higher fluid flow on the photocatalytic surface, thereby generating additional photons to catalyze the extra target chemical species in the photocatalyst 102. The curvature r can be formed during manufacture of the system 100 so that the light distributor 106 formed by the waveguides 150 can passively control light distribution. In another embodiment, the radius of curvature of the waveguide 150 can be dynamically controlled so that light delivery can be varied as the detected fluid flow profile varies.

The waveguides 150 themselves can have any shape and composition including, but not limited to, plates, cylinders (e.g., optical fibers) and foamed material. The shape of each waveguide 150 will influence the specific structure used to change the radius of curvature of the waveguide 150 to change the amount of light leakage from the waveguide 150 at selected areas in the reactor 100. As noted above, the radius of curvature of each waveguide 150 can be selected during manufacture, thereby allowing the resulting light distributor 106 to passively redistribute light. Alternatively, to change the radius of curvature dynamically and thereby provide active control over light distribution, the ends of the waveguides 150 may be connected to one or more actuators 152 that can twist the waveguides 150 to make their radius of curvatures tighter or looser. The actuators 152 are controlled by the controller 116 based on the desired irradiance profile.

Figure 3:
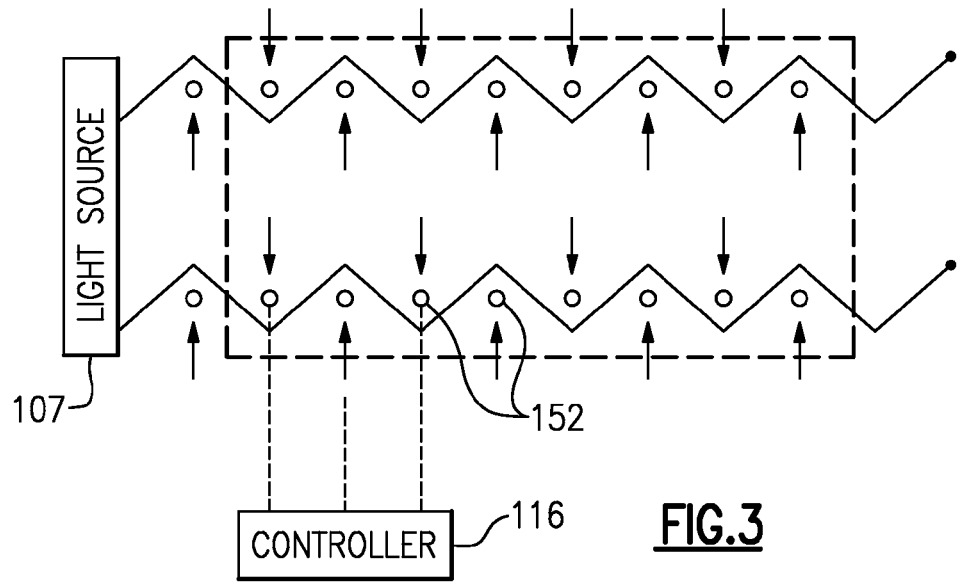
FIG. 3 is a representative diagram of another embodiment of the invention.

FIG. 3 illustrates another embodiment of the invention. In this embodiment, a cross-sectional dimension of the waveguide 150 can be varied to control light delivery to the item for making the irradiance profile uniform and/or for matching the irradiance profile with the fluid flow profile. Decreasing the cross-sectional area of a waveguide in, for example, a direction substantially perpendicular to a light propagation direction increases light leakage from the waveguide. Thus, waveguides in areas where the irradiance profile is low relative to other areas, and/or areas experiencing high fluid flow profiles may have their cross-sectional areas reduced to increase light leakage, and therefore increase the number of photons, in those areas. Like the other embodiments, the variations in this embodiment can be conducted either during manufacturing to form a static waveguide 150 or during operation of the system itself as a dynamic waveguide 150.

Devices used to decrease the cross-sectional area of the waveguide 150 may include, for example, devices that stretch and/or twist the waveguide (e.g., if the waveguide is made of a resilient material). In the illustrated dynamic embodiment, the waveguides 150 may be made of a resilient material and have fixed ends. At least one waveguide 150 is connected to actuators 152 that can move to stretch or release the waveguide 150 and thereby reduce or increase its cross-sectional area, respectively. The actuators 152 are controlled by the controller 116 so that the amount of stretching or releasing corresponds to the desired irradiance profile. The actuators 152 can move in any manner and in any direction that will facilitate stretching and releasing. In the illustrated embodiment, the actuators 152 are in the form of pins that are operated from above the pins to stretch or release the waveguide 150 in a given area.

In another example where the waveguides 150 are glass plates, for example, the cross-sectional area can be changed by changing a distance, and therefore an air gap, between the two plates. As noted above, matching the irradiance profile with the fluid flow profile can be conducted either as a single setting or as a dynamic process that changes as the fluid flow profile changes.

FIG. 4 illustrates yet another embodiment of the invention. Rather than changing the curvature or the cross-sectional area of the waveguides 150, this embodiment changes the refractive index of the waveguide cladding 154. As noted above, light leakage from the waveguide 150 is a function of the relative refractive indices of the core 151 of the waveguide 150 and its cladding 154. The core 151 generally has a higher refractive index, to varying degrees, than the cladding 154. By modifying the refractive index of the cladding 154 to a value closer to the refractive index of the core 151, the decrease in the difference between the two refractive indices increases the light leakage from the core 151 through the cladding 154. This modification can be conducted during waveguide manufacture to form the static light distributor 106.

In a dynamic light distributor 106, the cladding 154 of the waveguide 150 comprises a birefringent material whose light propagation characteristics can change based on characteristics of an electric or magnetic field 158 generated near the waveguide 150 by a field generator, which acts as the actuator 152. The controller 116 can therefore change the refractive index of the cladding 154 by modulating the characteristics of the field. Thus, increasing the refractive index of the cladding 154 can be used to increase the percentage of incident light leakage in areas where the irradiance profile is lower and/or areas where the fluid flow is highest on the photocatalytic surface. The refractive index can also be altered by other influences, such as temperature, pressure, or mechanical strain.

Figure 5:
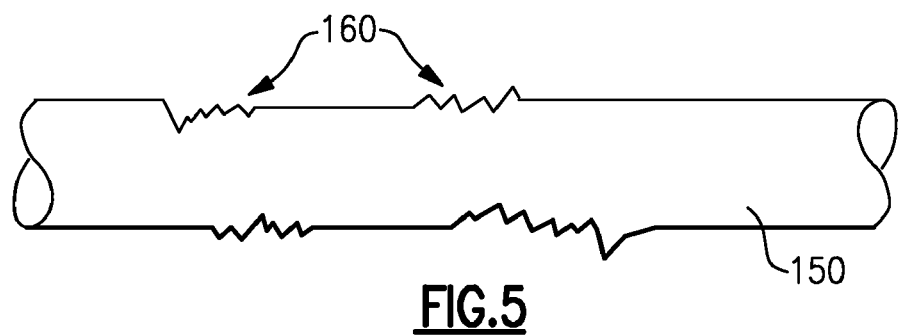
FIG. 5 is a representative diagram of yet another embodiment of the invention.

FIG. 5 illustrates yet another embodiment of the invention. The embodiment shown in FIG. 5 focuses on altering surface roughness, which in essence is altering local variations in curvature, in the waveguide 150 to control light leakage. For example, increasing the density and decreasing the size of local variations in the surface roughness of the waveguide may increase light leakage. Like the previous embodiments, certain waveguides 150 are selected for modification in surface roughness based on, for example, whether their irradiation profile needs to be increased to compensate for the higher profile closer to the light source 107 or whether the fluid flow profile is greater at a given area, thereby requiring increased light leakage in that area to optimize reactor efficiency. As shown in the Figure, roughened areas 160 on the waveguide surface may be disposed at selected areas during waveguide manufacture to change the light leakage in those areas.

The surface roughness can be controlled during waveguide manufacture by, for example, sandblasting or adding lumps of material to selected areas of the waveguide 150. In this embodiment, the waveguide 150 may contain core material only, with no cladding, to provide greater control over the light leakage characteristics during manufacture to form a static light distributor 106.

Figure 6:
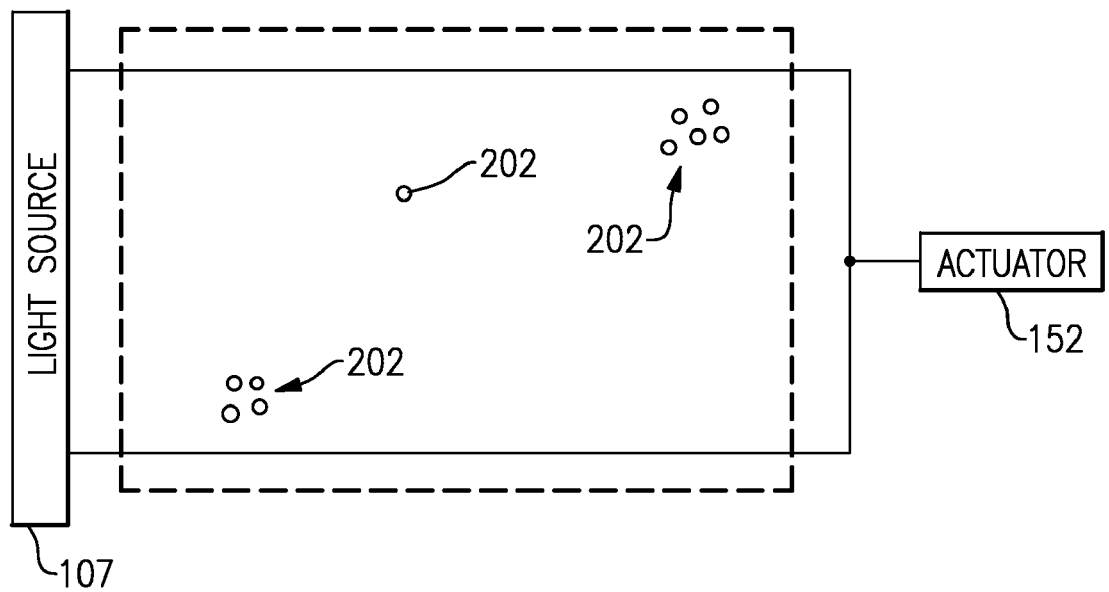
FIG. 6 is a representative diagram of another embodiment of the invention.

FIG. 6 illustrates a further embodiment of the invention. In this embodiment, it is assumed that the waveguide 150 has scattering centers 202 that affect light leakage from the waveguide 150 by scattering light out of the waveguide 150. For clarity, the waveguide 150 in this example is illustrated to have a plate-like shape; however, this embodiment can be applied to waveguides of any shape.

The local scattering centers 202 can be, for example, hollow regions (e.g., bubbles) or solid particles distributed within the waveguide material, with each scattering center comprising one bubble or particle that scatters light. The regions and/or particles that create the scattering centers can have any shape and size (e.g., regular, irregular, macroscopic, microscopic, etc.), depending on the desired light leakage effect. In one embodiment, the actuator 152 can vary the density and size of the scattering centers 202 in the waveguide as well as completely create and eliminate scattering centers 202. For example, increasing the density of the scattering centers 202 in areas away from the light source 107 will help compensate for any reduced internal irradiation, thereby achieving more uniform light delivery to the photocatalytic surface of the item 104. Similarly, increasing the density of scattering centers 202 in areas experiencing higher fluid flow profile values increases the light leakage, and therefore the number of photons, to accommodate the extra target chemical species due to the higher fluid flow. These scattering centers 202 may be formed during waveguide manufacture for a static light distributor 106.

In the dynamic light distributor example, the waveguide 150 may include one or more scattering centers formed of particles 202 that exhibit precipitation characteristics where the particles precipitate and dissolve back into the waveguide material 150 depending on the temperature of the environment. Local areas of phase change materials that respond to temperature changes can also act as temperature-controlled scattering centers similar to the precipitation particles. The controller 116 can therefore modify the irradiance profile by changing the temperature in different areas of the waveguide 150. In another example, the waveguide 150 may include particles 202 of liquid crystal material whose light transmission characteristics are controlled by an orientation and/or strength of an electric field. Thus, the controller 116 can change the light leakage characteristics of the scattering centers by changing the electric field, thereby changing the orientation of the liquid crystal particles 202.

In the embodiments described above, the waveguides 150 can have any shape and are not limited to the cylindrical shapes as shown. For example, the waveguides can be formed as straight or curved cylinders, plates, optical foam, or fibers having a circular, curved or polygonal cross-section.

FIG. 7 illustrates a side view of yet another embodiment of the invention applicable to systems where the light is not guided by total internal reflection like the waveguide examples described above. In this embodiment, the irradiance profile is controlled by one or more reflectors 210 near the light source 107. The reflectors 210 can be shaped to achieve a uniform irradiance profile and/or match the fluid flow profile. In one embodiment, the reflector 210 is made of a resilient reflective material that can be bent and reshaped based on the detected fluid flow profile so that the reflector 210 causes the irradiance profile to match the fluid flow profile. Alternatively, or in addition, the controller 116 can reorient selected reflectors 210 to reflect light from the light source 107 in different directions at any given time using known adaptive optics techniques.

FIG. 8 illustrates a side view of another embodiment of the invention applicable to systems that do not use total internal reflection to guide light. In this embodiment, one or more lenses 220 are used to guide light from the light source 107 to the photocatalytic surface. The shape and/or orientation of the lenses 220 can modify the irradiance profile to improve uniformity and/or match a fluid flow profile. The orientation of the lenses 220 can be controlled by the controller 116 based on the desired irradiance profile. Note that lenses 220 and reflectors 210 can be used together in the same reactor 100 to provide greater control over the irradiance profile.

Regardless of the specific embodiment used to control the irradiance profile of the light delivery system, the inventive system can be used to match an irradiance profile with a fluid flow profile either statically (where the irradiance profile reflects the fluid flow profile at a selected point in time) or dynamically (where the irradiance profile changes as the fluid flow changes) and can also be used to compensate for lower irradiance profile values in areas of the reactor 100 away from the light source 107.

Although the embodiments described above have been described as separate embodiments, it is possible to combine two or more embodiments in the same reactor 100 without departing from the scope of the invention. Also, even though the above examples describe a light delivery system for a photoreactor, the light delivery system can be used in other applications without departing from the scope of the invention. Those of ordinary skill in the art will recognize that applications other than photoreactors may desire light delivery systems that have a uniform irradiance profile and/or have a profile that can be controlled to match a desired irradiance profile. Further, those of ordinary skill in the art will recognize that the irradiance profile can be controlled using methods and systems other than those specifically set forth above without departing from the scope of the invention.

It should be understood that various alternatives to the embodiments of the invention described herein may be employed in practicing the invention. It is intended that the following claims define the scope of the invention and that the method and apparatus within the scope of these claims and their equivalents be covered thereby.

What is claimed is:

1. A method of controlling light delivery to a photocatalytic surface, comprising:
    emitting light from a light source to a photocatalytic surface;
    controlling how a light distributor modifies an irradiance profile of the light before the light reaches the photocatalytic surface based upon data from at least one of a fluid flow sensor or a light sensor; and
    comparing the irradiance profile of the light with a desired irradiance profile, and commanding the light distributor to modify the irradiance profile to match the desired irradiance profile.

2. The method of claim 1, wherein the desired irradiance profile is a substantially uniform irradiance profile.

3. The method of claim 1, further comprising monitoring a fluid flow profile as the data.

4. The method of claim 1, further comprising controlling an amount of light leakage from at least one of a plurality of waveguides of the light distributor.

5. The method of claim 4, further comprising controlling a radius of curvature of the at least one of the waveguides.

6. The method of claim 4, further comprising controlling a cross-sectional area of the at least one of the waveguides.

7. The method of claim 4, further comprising controlling a characteristic of at least one scattering center of the plurality of waveguides.

8. The method of claim 7, further comprising creating, eliminating, or modifying said at least one scattering center.

9. The method of claim 7, further comprising controlling at least one of a temperature, an electric field, or a magnetic field relative to particles, bubbles, or liquid crystal material of said at least one scattering center.

10. The method of claim 1, further comprising controlling at least one of a shape, a position, or an orientation of a reflector associated with the light source.

11. The method of claim 1, further comprising controlling at least one of a shape, a position, or an orientation of a lens associated with the light source.

12. The method of claim 1, including controlling how the light distributor modifies the irradiance profile based upon data from the fluid flow sensor and the light sensor.

13. The method of claim 1, including controlling how the light distributor modifies the irradiance profile based upon data from the fluid flow sensor.

14. The method of claim 1, including controlling how the light distributor modifies the irradiance profile based upon data from the light sensor.

15. The method of claim 1, further comprising controlling an actuator that is coupled to the light distributor to influence the light distributor.

16. The method of claim 1, further comprising influencing at least one characteristic selected from a radius of curvature of the light distributor, a cross-sectional area of the light distributor, or a refractive index of the light distributor.

17. The method of claim 1, further comprising influencing at least one characteristic selected from a temperature, a pressure, a mechanical strain, an electric field, or a magnetic field to influence the amount of light leakage from the light distributor.

18. A method of controlling light delivery to a photocatalytic surface, comprising:
    emitting light from a light source to a photocatalytic surface;
    controlling how a light distributor modifies an irradiance profile of the light before the light reaches the photocatalytic surface based upon data from at least one of a fluid flow sensor or a light sensor; and
    controlling an amount of light leakage from at least one of a plurality of waveguides of the light distributor, wherein at least one of said plurality of waveguides comprises a core having a first refractive index and a cladding having a second refractive index, and wherein the step of controlling the amount of light leakage comprises controlling a relationship between the first and second refractive indices.

19. The method of claim 18, further comprising controlling at least one of a temperature, a pressure, a mechanical strain, an electric field, or a magnetic field in an area near said at least one waveguide.

* * * * *